United States Patent [19]
Lefebvre et al.

[11] 4,302,286
[45] Nov. 24, 1981

[54] REACTOR VESSEL IN-SERVICE INSPECTION ASSEMBLY AND ULTRASONIC CENTERING DEVICE

[75] Inventors: Bernard J. Lefebvre; William H. Krueger, both of Pittsburgh, Pa.

[73] Assignee: Westinghouse Electric Corp., Pittsburgh, Pa.

[21] Appl. No.: 32,799

[22] Filed: Apr. 24, 1979

[51] Int. Cl.³ .......................................... G21C 17/00
[52] U.S. Cl. .................................. 376/249; 73/634; 367/96; 376/252
[58] Field of Search ............... 176/19 R; 367/151, 96, 367/95, 117; 73/634

[56] References Cited

U.S. PATENT DOCUMENTS

| | | | |
|---|---|---|---|
| 2,743,429 | 4/1956 | Erdman et al. | 367/96 |
| 2,801,403 | 7/1957 | Keitz | 340/1 |
| 3,028,752 | 4/1962 | Bacon | 73/627 |
| 3,532,182 | 10/1970 | Buoyoucous | 367/151 |
| 3,732,946 | 5/1973 | McKnight et al. | 367/151 |
| 3,743,429 | 4/1956 | Erdman et al. | 340/1 |
| 3,809,607 | 5/1974 | Murray et al. | 176/19 R |
| 3,907,062 | 9/1975 | Brigham et al. | 367/151 |
| 3,943,756 | 3/1976 | Aubert et al. | 176/19 R |
| 3,988,922 | 10/1976 | Clark et al. | 176/19 R |
| 4,083,225 | 4/1978 | Day et al. | 73/19 |
| 4,131,018 | 12/1978 | Muller et al. | 176/19 R |

FOREIGN PATENT DOCUMENTS 2855207  2/1979  Fed. Rep. of Germany ...... 367/151

*Primary Examiner*—S. A. Cangialosi
*Attorney, Agent, or Firm*—Daniel C. Abeles

[57] ABSTRACT

A reactor vessel in-service inspection assembly (17) having an improved positioning device (80) for properly and repeatedly locating the inspection transducers (75) of the assembly within a hollow portion of the reactor vessel cavity. An acoustic transducer of the positioning device of this invention is affixed to the positioning arm (40) of the inspection transducers (75). The positioning transducer is operable to generate and simultaneously, radially direct acoustic signals around the circumference of the hollow portion of the vessel cavity and receive the signals reflected off of the cavity walls at a location within the hollow cavity. Means are provided for monitoring the received signals as a function of time. The in-service inspection assembly transducer positioning arm is arranged to automatically move in response to the monitored difference in the time of reception of the received signals to locate the positioning transducer at a preestablished location within the hollow portion of the reactor cavity.

19 Claims, 5 Drawing Figures

REACTOR VESSEL IN-SERVICE INSPECTION ASSEMBLY AND ULTRASONIC CENTERING DEVICE

BACKGROUND OF THE INVENTION

This invention pertains generally to acoustic positioning systems and more particularly to reactor vessel in service inspection manipulator positioning systems.

Commercial power nuclear reactors include a vessel which is generally a cylindrical metallic member having a top flange welded to it, with a plurality of nozzles attached to and extending through the vessel wall. Numerous welds are used in fabricating the vessel, in joining the flange to the cylindrical portion of the vessel, as well as in providing the inlet and outlet nozzles. While the reactor vessel is itself encased in a thick concrete containment area in the plant, the structural integrity of the reactor vessel must be assured.

The weld areas of the reactor vessel are inspected before the vessel is placed in use, and in-service inspection of the vessel weld areas is desirable and required by Governmental regulation. Such in-service inspections are usually carried out in an underwater, radioactive environment with remote control operation, while maintaining a high degree of precision of placement and movement of the inspection tooling.

As a practical matter, the tooling designed for this purpose must have the capability of accommodating a variety of sizes of reactor vessels.

A number of in-service inspection manipulators exist in the art, such as the manipulator taught in U.S. Pat. No. 3,809,607, to T. R. Murray et. al., issued May 7, 1974. Manipulators of this type generally include fixturing adapted to be keyed on a predetermined location on the reactor vessel. The fixturing is generally employed to support the manipulator and serve as a reference for a number of encoders which track the location of inspection transducers so that a complete and coordinated map of the vessel and its appendages can be made. Normally, ultrasonic transducers are employed to perform the nondestructive inspection mapping. The transducers are generally supported, cantilevered off of a central column as described in the above noted patent. The inspection transducers' outputs with respect to their position in the vessel are recorded as the transducers are scanned over the required surface of the vessel and its appendages to satisfy the volumetric examination required by Governmental regulation. This record is then evaluated and compared with previous mappings to determine the state of the vessel.

It can be appreciated therefore, that in order for any volumetric examination to have value it must be made to exactly correspond to previous mappings. This requires that the transducers be moved in a manner to replicate previous examinations. Therefore, exact positioning and scanning of the transducers is not only desirable, but necessary to the success of the examination. Any improvement in accomplishing replication of the scanning process therefore significantly enhances the reliability of the result that is achieved. Normally, inspection manipulators of this type have a number of movable joints each having an encoder which provides an output representative of the relative positioning of its corresponding connecting elements or limbs. The combination of the encoder's outputs together with the rigidity of the manipulator generally assures the accuracy of positioning the transducers around the reactor vessel. However, when the manipulator's various joints are extended in the course of an in-service inspection in an irradiated reactor vessel environment, the exact mechanical positioning of the inspection transducers by the manipulator as reflected by the encoder outputs may vary slightly from the transducers' true position with respect to the vessel.

Therefore, to assure the accuracy and exact duplication of each scan performed during a volumetric examination, it is desirable to have an independent position indication system which can assure the exact location of the transducer extension of the manipulator arm within the reactor vessel cavity. More particularly, it is desirable to have such a position indication and location device for exactingly positioning the scanning transducers within the apertures of the reactor vessel nozzles.

SUMMARY OF THE INVENTION

Briefly, this invention provides an improved reactor vessel in-service inspection assembly having an elongated inspection transducer arm (40), wherein the improvement comprises means for positioning the arm (40) at a predetermined location within a hollow portion of the reactor vessel cavity. The positioning means includes means (80) affixed to the positioning arm for generating, simultaneously, radially, acoustic signals around the circumference of the hollow portion of the vessel cavity and receiving the signals reflected off of the cavity walls, at a location within the hollow portion. A monitor is provided for processing the transducer outputs as a function of time. Desirably the positioning arm mechanism (40) is arranged to be responsive to the monitored difference in time of reception of the received signals to position the arm at a pre-established location within the hollow portion of the reactor vessel cavity.

Desirably, in the preferred embodiment, the generating and receiving means includes a transducer located coincident with the axis of the positioning arm and having a generating face or reflector (86) which radially directs the acoustic signals around the circumference of the hollow portion and redirects the reflected signals to the transducer. In one preferred form, the reflector or generating face is shaped as a pyramid to enhance reception of the monitored outputs for control of the positioning arm. In the case where the pre-established location is centered within the hollow cavity, the positioning controller for the transducer arm is programmed to locate the arm to minimize the difference in time of reception between the received acoustic signals monitored.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

Figure 1:
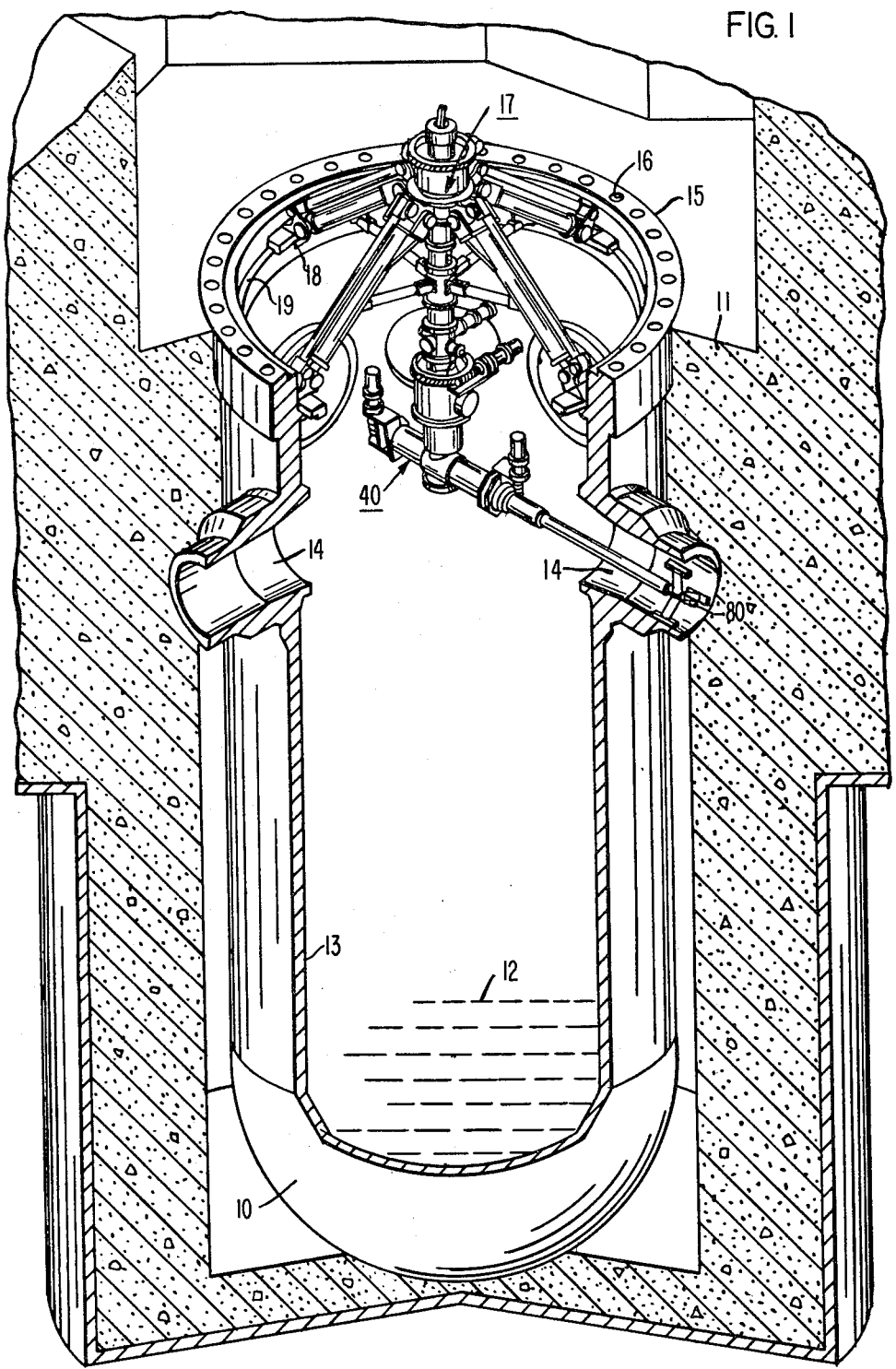
FIG. 1 is a perspective view of a portion of a reactor in-service inspection assembly shown in place in a reactor vessel and illustrating a nozzle scanner incorporating the acoustic positioning device of this invention.

The invention can best be appreciated by reference to the exemplary embodiments shown in the drawings in which FIG. 1 illustrates a nuclear reactor vessel 10 in place within a containment concrete encasement 11. The concrete encasement 11 surrounds and encompasses the bottom portion of the reactor vessel, while the top portion of the concrete encasement defines a means of providing a pool of borated water 12 within and about the reactor vessel. The vessel 10 comprises a generally cylindrical shell portion 13 having a plurality of inlet and output nozzles 14 extending through the sidewalls thereof. A sealing flange 15 is disposed at the upper end of the cylindrical shell portion 13. A plurality of bolt holes 16 are provided in the sealing flange to permit the sealing of the reactor vessel by means of a header, not shown. The in-service inspection assembly 17 is shown in place supported by the reactor vessel. For the purpose of illustration, the inspection assembly illustrated in FIG. 1 is fitted with a nozzle scanner assembly 40 incorporating the positioning system of this invention. The inspection assembly 17 is mounted upon and supported by accurately positioned keyways 18 provided in the reactor vessel internal support flange 19. The keyways 18 are machined to provide a positional frame of reference with respect to all vessel dimensions.

Figure 2:
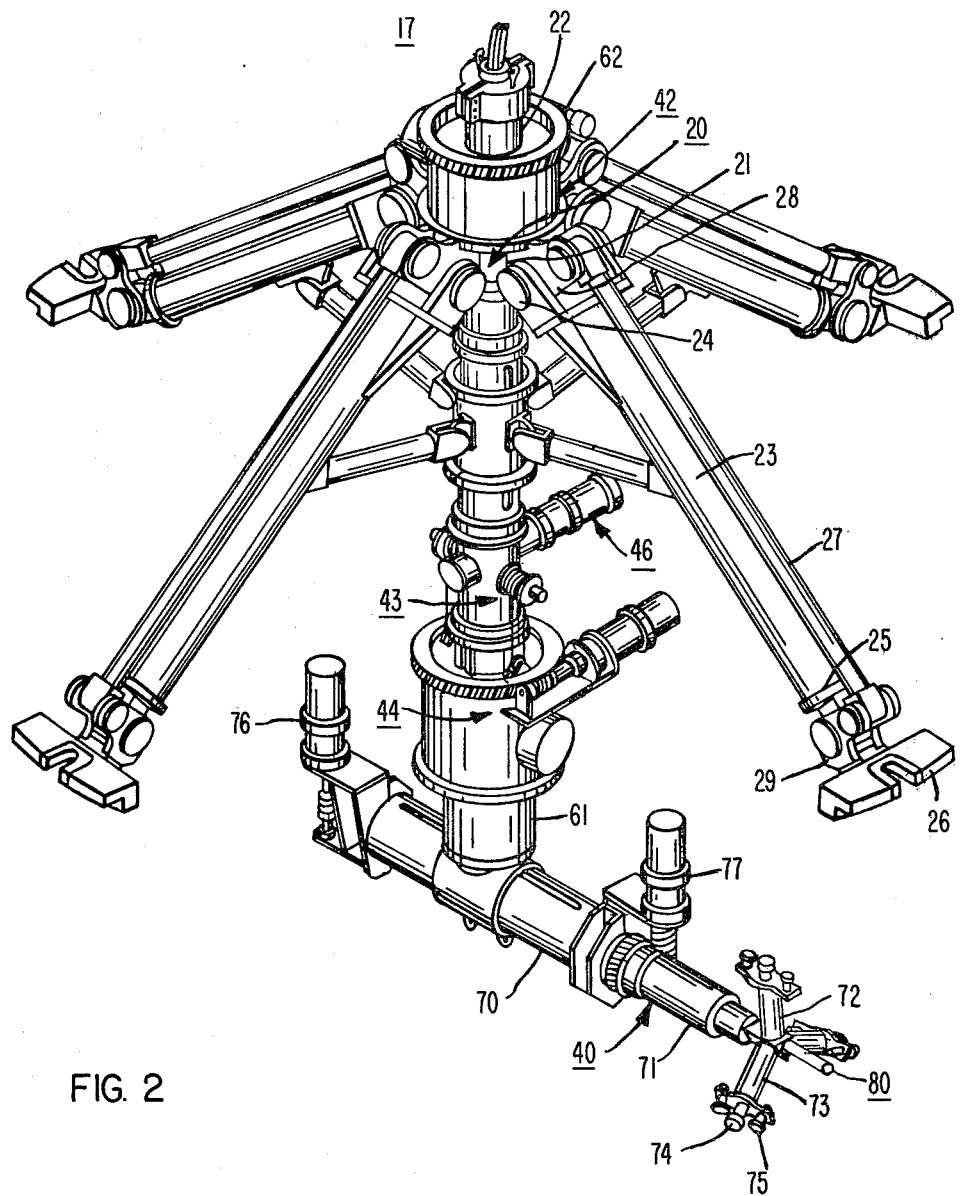
FIG. 2 is a side perspective of the nozzle scanner of the present invention illustrated in FIG. 1.

As shown in FIG. 2, the inspection assembly 17 comprises a positioning and support assembly 20 which includes a central body portion or weldment 21 mounted on a tubular central column 22, which, with the assembly 17 in place, extends along the longitudinal axis of the reactor vessel. For nozzle scanning applications the central column 22 only need extend as far as the nozzles in the vessel. A plurality of radial directed support arms 23 extend from the weldment or central body portion 21 and are pivotally connected thereto at pivot point 24. The other end 25 of the respective support arms 23 are adapted with support shoes 26 which fit the reactor vessel key ways 18. Tie rods 27 are coupled at ends 28 to the central body portion 21 and at the other end 29 to the shoe 26 to assure that the seating surface of each shoe is raised and lowered in unison and that each shoe sealing surface remains parallel to each other. This insures the accuracy of the positional frame of reference of the inspection assembly relative to the vessel. All positional measurements are taken with respect to the reactor vessel key ways and the inspection assembly, to the extent mechanically feasible, is accurately maintained with respect to this positional frame of reference.

The movable inspection assemblies include a flange scanner assembly which is not shown, the nozzle scanner assembly 40, and a vessel shell scanner assembly all of which are shown in more detail in U.S. Pat. No. 3,809,607 to T. R. Murray et al., issued May 7, 1974. Vertical movement of the nozzle scanner 40 and vessel scanner is achieved by the main carriage vertical drive 43 and the main carriage assembly 44. The main carriage assembly 44 provides the means to rotate the nozzle scanner and vessel scanner relative to the central column.

The nozzle scanner assembly 40 comprises a radially extending body portion 70 which is retained by a clamping fixture 61 so that the body portion 70 extends radially out from the longitudinal axis of the central column. The position at which the clamping fixture engages the body portion can be used to vary the radial extent of the assembly 40 to permit use with various vessel diameters. A telescoping tube portion 71 extends from one end of the body portion 70 and a three-pronged nozzle fitting member 72 is disposed at the extending end of the telescoping tube portion 71. The three individual arms or prongs 73 of member 72 are spring loaded with a nozzle wall abutting bearing 74 and a nozzle inspection ultrasonic transducer array 75 is disposed at the end of each respective arm 73. A nozzle longitudinal feed electric drive 76 is used to drive a worm gear set and acme screw thread extending member which is not shown, but which is disposed within the body portion 70 and extends from the electric drive 76 to the telescoping tube portion 71 to actuate and effect extension and retraction of the telescoping tube portion when the nozzle scanner is positioned within the nozzle. The drive 76 can position the transducer array 75 at any selected position within the nozzle as far as the safe end weld inspection requires. The drive 76 has an integrally mounted encoder for position indication as do all electric drive means utilized in the inspection assembly 17, with the exception of the drive 46 which has an externally mounted encoder which reads a rack. A nozzle rotary electric drive 77 is mounted on the body portion 70 and is used to rotate the nozzle fitting member 72 and the supported transducer arrays 75 about the nozzle. The drive 77 is connected to a worm gear set, not shown, and an integrally mounted encoder is associated with drive 77 for angular position indication.

The spring loaded arm 73 serve to accurately space the transducer arrays 75 from the nozzle inside wall and will compensate for any ovality of the nozzle. The end bearing or balls 74 facilitate rotation of the three-pronged nozzle fitting member 72. The scan is carried out by rotating member 72 one revolution at a given longitudinal position, indexing longitudinal drive 76 and then rotating member 72 in a reverse direction, and so on.

In order to accurately perform the measurements, the mechanical positioning device formed by the three-pronged nozzle fitting member 72 must be positioned on the center line of the nozzle. In its preferred embodiment, this invention provides an improved positioning device for precisely locating the three-pronged nozzle fitting member 72 on the reactor vessel nozzle center line.

In accordance with the preferred embodiment of this invention, an additional ultrasonic transducer 80 is affixed to the end of the three-pronged nozzle fitting member 72 and arranged to direct ultrasonic energy simultaneously, radially, toward the wall of the nozzle around its circumference and receive the signals reflected off of the nozzle walls. The received signals are monitored as a function of time and the inspection assembly is manipulated in response to the monitored difference in time of reception of the received signals to position the nozzle fitting member 72 at its preselected location on the central axis of the nozzle. If the nozzle was circular in cross-section, the reflected signals received by the positioning transducer 80 would be coincident in time when the transducer was located about the central axis of the nozzle.

Figure 3:
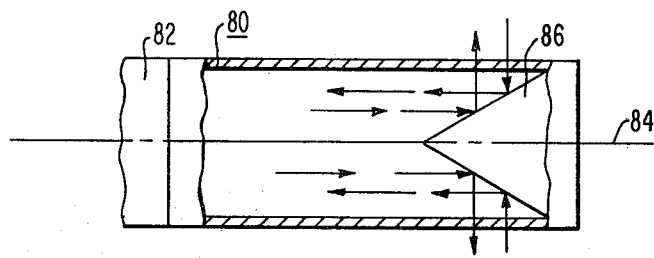
FIG. 3 is a side perspective of the positioning transducer and reflector assembly of one embodiment of this invention, with portions thereof cut away for clarity.

A number of transducers with cylinder generating faces or conical reflectors which can be used for the transducer 80 are taught in patent application Ser. No. 4,083,225 to C. K. Day et al., issued Apr. 11, 1978. Such a transducer is illustrated in FIG. 3 and includes an ultrasonic transmitter and receiver 82 which has as its basic functioning component a piezoelectric element which is orientated centered about the nozzle axis 84, to direct substantially parallel acoustic signals to a conical reflector 86 which is located in juxtaposition along the common axis 84. The conical sides of the reflector 86 are inclined at a 45° angle to reflect the incoming signals from the transducer 82, 90°, radially out towards the walls of the nozzle. If the transducer assembly 80 is properly aligned along the axis 84 and the nozzle is truly cylindrical with a circular cross-section, the reflected signals imparted back to the transducer 82, by way of the reflector 86, which were generated simultaneously, will be received at the same time. Therefore, the monitored return signals can be employed to identify the relative position of the transducer assembly 80 and the nozzle fitting member 72 and its associated inspection transducers 75. Locating the telescoping tube portion 71 off center will give rise to a difference in time of reception of the reflected signals which can be calibrated to indicate the exact location of the scanner assembly 40 relative to the walls of the vessel nozzle. The output of the scanner assembly can be presented on an A scan display for manual positioning of the assembly or fed into a comparison network operable to automatically position the scanner assembly 40 to minimize the difference in time or reception between the received signals. Electronic controls for close loop manipulation in this manner are readily known in the art and examples thereof can be found in U.S. Pat. No. 2,743,429, issued Apr. 24, 1956 and U.S. Pat. No. 3,943,756, issued Mar. 16, 1976.

Figure 4:
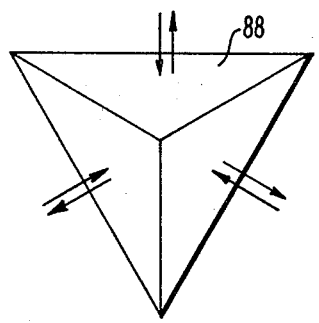
FIG. 4 is a top perspective of one embodiment of the reflector assembly illustrated in FIG. 3.
Figure 5:
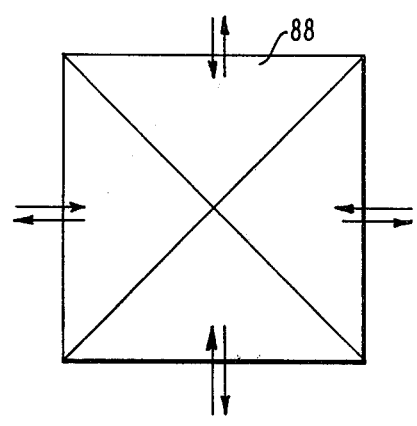
FIG. 5 is a top perspective view of a second embodiment of the reflector assembly illustrated in FIG. 3.

In the preferred form, the reflector 86 is constructed as a pyramid as illustrated in FIGS. 4 and 5, which respectively show top views of a three-sided and a four-sided pyramid reflector. The pyramid shape is desirable to maximize the intensity of the return signals.

Thus, it should be appreciated that in accordance with this invention sound waves originating at the transducer assembly 82, directed radially to the nozzle wall will be reflected off the inside surface of the nozzle back to the positioning transducer of this invention and can be represented by separate indications on an A scan display. The positioning transducer can thus be centered in a cavity of circular cross-section by manipulating the transducer until the various A scan indications are coincident. If the cavity is not circular in cross-section, the proportional difference between A scan indications is employed to determine the center of the cavity.

Where a conical reflector is employed to radially direct the transducer, one peaked signal can be used to determine the center of a cavity of circular cross-section. Where a pyramid or conical reflecting surface is employed, its sides need not be flat. A concave surface can be employed to focus the acoustic signals for maximum intensity depending upon the geometry of the hollow section in which the transducer is employed.

While a three-sided pyramid would be desirable to maximize the intensity of the received signal, in applications where the manipulator positions the transducer by moving along lines parallel to the X and Y planes, a four-sided pyramid is advantageous. The four reflected signals monitored can then be directly employed as the control signals for activating the manipulator to minimize the difference in time of reception of the received signals.

Accordingly, an improved inspection assembly is provided with an ultrasonic positioning device that accurately maintains the positioning of the inspection transducers along a desired axis, without disturbing the orientation of the inspection transducers.

We claim:

1. An improved reactor vessel in-service inspection assembly having an inspection transducer positioning arm wherein the improvement comprises means for locating the positioning arm at a pre-established location within a hollow portion of the reactor vessel cavity wherein the locating means includes:
    means affixed to the positioning arm for generating and simultaneously, radially, directing acoustic signals around the circumference of the hollow portion of the vessel cavity and receiving the signals reflected off of the cavity walls and redirected to the location from which the signals were originally, radially directed, at a position within the hollow portion wherein the generating and receiving means comprises an acoustic transducer and reflector wherein the reflector is constructed to radially direct the acoustic signals generated by the transducer to the walls of the hollow portion of the reactor vessel cavity and redirect the acoustic energy reflected off the cavity walls back to the reflector to the transducer;
    means for monitoring the received signals as a function of time; and
    means for positioning the arm in response to the monitored difference in time of reception of the received signals, at the pre-established location within the hollow portion of the reactor vessel cavity.

2. The reactor vessel in-service inspection assembly of claim 1 wherein the generating and receiving means comprises an acoustic transducer having a cylindrical acoustic generating face.

3. The reactor vessel in-service inspection assembly of claim 2 wherein the axis of revolution of the cylindrical generating face is coincident with the axis of the positioning arm.

4. The reactor vessel in-service inspection assembly of claim 1 wherein the reflector is shaped as a cone.

5. The reactor vessel in-service inspection assembly of claim 1 wherein the reflector is shaped as a three-sided pyramid.

6. The reactor vessel in-service inspection assembly of claim 1 wherein the reflector is shaped as a four-sided pyramid.

7. The reactor vessel in-service inspection assembly of claim 1 wherein the reflector is positioned on the axis of the positioning arm.

8. The reactor vessel in-service inspection assembly of claim 6 wherein the means for locating the arm moves the arm in a forward and reverse direction along lines parallel to both the X and Y axes.

9. The reactor vessel in-service inspection assembly of claim 1 or 8 wherein the means for locating the arm positions the arm at the pre-established location automatically in response to the monitored difference in time of reception of the received signals.

10. The reactor vessel in-service inspection assembly of claim 1 wherein the pre-established location is substantially at the center of the hollow portion of the reactor vessel cavity.

11. The reactor vessel in-service inspection assembly of claim 10 wherein the means for locating the arm moves the arm in a direction to minimize the time difference between received signals.

12. Apparatus for identifying a pre-established location within a hollow cavity comprising:
   means for generating and simultaneously, radially directing acoustic signals around the circumference of the cavity and receiving the signals reflected off of the cavity walls and redirected to the location from which the signals were originally, radially directed, at a position within the cavity wherein the generating and receiving means comprises an acoustic transducer and reflector wherein the reflector is constructed to radially direct the acoustic signals generated by the transducer to the walls of the cavity and redirect the acoustic energy reflected of the cavity walls back to the reflector to the transducer;
   means for monitoring the received signals as a function of time; and
   means for positioning the generating and receiving means in response to the monitored difference in time of reception of the received signals, at the pre-established location within the cavity.

13. The apparatus of claim 12 wherein the reflector is constructed as a pyramid.

14. The apparatus of claim 13 wherein the reflector is a three-sided pyramid.

15. The apparatus of claim 13 wherein the reflector is a four-sided pyramid.

16. The apparatus of claim 15 wherein the means for positioning the generating and receiving means moves the generating and receiving means in a forward and reverse direction along lines parallel to both the X and Y axes.

17. The apparatus of claim 12 or 16 wherein the means for positioning the generating and receiving means positions the generating and receiving means at the pre-established location automatically in response to the monitored difference in time of reception of the received signals.

18. The apparatus of claim 12 wherein the pre-established location is substantially at the center of the cavity.

19. The apparatus of claim 18 wherein the means for positioning the generating and receiving means moves the generating and receiving means in a direction to minimize the time difference between received signals.

* * * * *